United States Patent [19]
Goldstein

[11] Patent Number: 5,247,176
[45] Date of Patent: Sep. 21, 1993

[54] INFRARED LASER POLARIMETER

[75] Inventor: Dennis H. Goldstein, Niceville, Fla.

[73] Assignee: The United States of America as represented by the Secretary of the Air Force, Wright-Patterson Air Force Base, Ohio

[21] Appl. No.: 733,999

[22] Filed: Jul. 22, 1991

[51] Int. Cl.⁵ .............................. G01N 21/21
[52] U.S. Cl. ..................... 250/338.1; 356/368; 356/367
[58] Field of Search ........... 250/338.1; 356/364, 356/365, 366, 367, 369, 368

[56] References Cited

U.S. PATENT DOCUMENTS

| | | | |
|---|---|---|---|
| 3,155,762 | 11/1964 | Gillham. | |
| 4,306,809 | 12/1981 | Azzam | 356/369 |
| 4,681,450 | 7/1987 | Azzam | 356/367 |
| 4,818,881 | 4/1989 | Tanton et al. | 250/338.1 |
| 4,884,886 | 12/1989 | Salzman et al. | 356/367 |
| 5,045,701 | 3/1991 | Goldstein et al. | 250/339 |

OTHER PUBLICATIONS

*Polarized Light*, by W. A. Shurcliff, Harvard View Press, Boston, (1962), Appendix 2, pp. 165-171.

*Matrix Theory of Photoelasticity*, by P. S. Theocaris, Springer-Verlag, Berlin (1979), p. 60, table 4.3.

"Photopolarimetric measurement of the Mueller matrix by Fourier analysis of a single detected signal", RMA Azzam, Opt. Lett. 2:6, 148 (1978).

"Measurement of Polarized light interactions via the Mueller Matrix", Thompson et al, Appl. Opt. 19:8, 1323-1332 (Apr. 15, 1980).

"Error Analysis of a Mueller matrix polarimeter", Goldstein et al, J. Opt. Soc. Am. 1(A):4, 693 (Apr. 1990).

*Primary Examiner*—Carolyn E. Fields
*Attorney, Agent, or Firm*—Bobby D. Scearce; Thomas L. Kundert

[57] ABSTRACT

An infrared laser polarimeter system for measuring the Mueller matrix of a sample is described which comprises, a infrared laser source for projecting a beam of preselected wavelength (preferably 3-14 μm) along an optical axis, at least one polarizing element disposed along the axis for linearly polarizing the beam and producing an output beam for analysis, first and second rotatable optical retarders disposed between the source and polarizing element and defining a sample region therebetween, the second retarder being rotated at least five times that for the first retarder, an integrating sphere, and a detector for analyzing the output beam.

7 Claims, 3 Drawing Sheets

INFRARED LASER POLARIMETER

RIGHTS OF THE GOVERNMENT

The invention described herein may be manufactured and used by or for the Government of the United States for all governmental purposes without the payment of any royalty.

CROSS REFERENCE TO RELATED APPLICATION

The invention described herein is related to copending application Ser. No. 07/413,414 filed Sep. 27, 1989, now U.S. Pat. No. 5,045,701, entitled "Infrared Spectropolarimeter".

BACKGROUND OF THE INVENTION

The present invention relates generally to infrared polarimeters, and more particularly to an infrared laser polarimeter system for measuring polarization properties and electro-optic and magneto-optic constants of infrared transmissive materials.

Existing polarimeters are generally configured to use polarization information to measure single quantities which are not necessarily descriptive of material properties of a sample. A Mueller matrix photopolarimeter for making scattering ellipsometry measurements was described by Thompson et al ("Measurement of polarized light interactions via the Mueller matrix", Appl Opt 19, 1323-1332 (1980)). This instrument is complicated, requires four Pockel cell modulators and multiple lock-in amplifiers and, by the nature of the data acquisition process, has limited accuracy. Azzam (U.S. Pat. No. 4,681,450) described an instrument for measuring the Stokes vector and which is capable of measuring the Mueller matrix of a sample, but is limited to the visible spectrum because the design requires visible light detectors. No other known instruments are configured for measuring the Mueller matrix of materials in transmission.

The invention solves or substantially reduces in critical importance problems with prior art polarimeters by providing an infrared laser polarimeter for measuring polarization properties of infrared transmissive materials and fundamental electro-optic and magneto-optic constants of these materials. The invention measures the Mueller matrix to acquire a complete description of the polarization properties of the sample, and includes an infrared laser source, a series of rotatable infrared polarization elements and an infrared detector. The sample is placed between two sets of rotatable polarization elements which may comprise combinations of a linear polarizer and a linear retarder. The Product of the method and subsequent data reduction is a 4×4 Mueller matrix containing information about the polarization properties of the sample (e.g., retardance, diattenuation, depolarization, scattering) except absolute phase. The infrared laser Polarimeter of the invention provides polarization and material property information as does the infrared spectropolarimeter described previously, but the invention provides the information at specific selected wavelengths and with greater spectral resolution at those wavelengths than that provided by the infrared spectropolarimeter.

It is therefore a principal object of the invention to Provide an infrared laser Polarimeter system for measuring polarization properties of materials.

It is a further object of the invention to provide an infrared laser polarimeter system and method for measuring the fundamental electro-optic and magneto-optic constants of infrared transmissive materials.

These and other objects of the invention will become apparent as a detailed description of representative embodiments proceeds.

SUMMARY OF THE INVENTION

In accordance with the foregoing principles and objects of the invention, an infrared laser polarimeter system for measuring the Mueller matrix of a sample is described which comprises, a infrared laser source for projecting a beam of preselected wavelength (preferably 3-14 $\mu$m) along an optical axis, at least one polarizing element disposed along the axis for linearly polarizing the beam and producing an output beam for analysis, first and second rotatable optical retarders disposed between the source and polarizing element and defining a sample region therebetween, the second retarder being rotated at least five times that for the first retarder, and a detector for analyzing the output beam.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
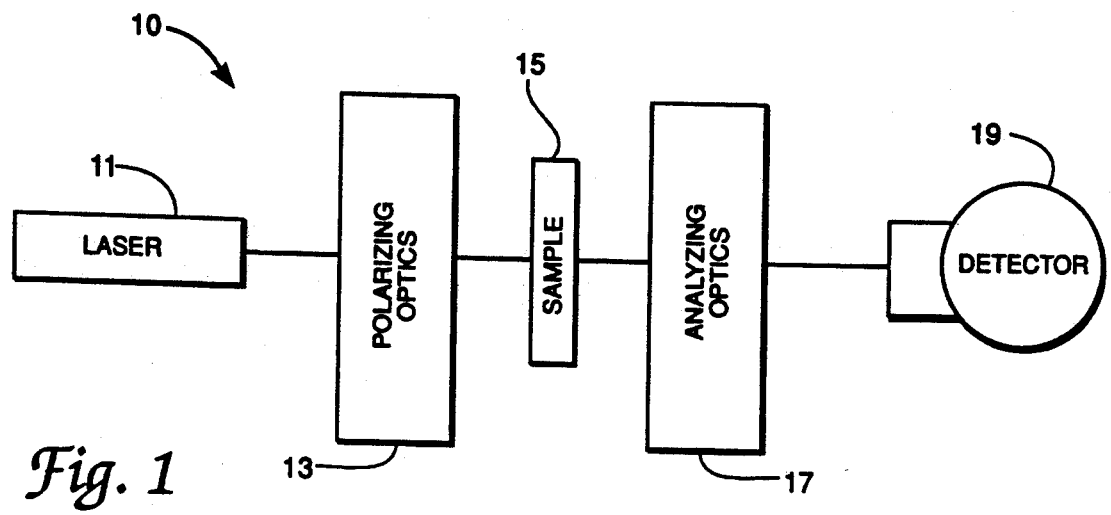
FIG. 1 is a block diagram of the essential components of an infrared laser polarimeter system according to the invention.

Referring now to the drawings, FIG. 1 shows in block diagram form the essential components of a polarimeter system 10 according to the invention. System 10 comprises five basic sections, viz., laser source 11, polarizing optics 13, sample region 15, analyzing optics 17 and infrared detector 19. In the analysis of materials according to the principal function of the invention, laser source 11 may generally comprise any low power laser source such as $CO_2$, CO, HeNe or HF type operating in the spectral region from about 3-14 microns ($\mu$m), which region is of interest for evaluating materials used as elements of optical processing systems, infrared optical systems or thermal imaging systems. Polarizing optics 13 may generally comprise a linear polarizer and a quarter waveplate. Analyzing optics 17 may comprise a quarter waveplate (or other suitable retarder as suggested below) followed by a linear polarizer. Polarization sensitivity of detector 19 is not important since the orientation of the final polarizer does not change.

Figure 2:
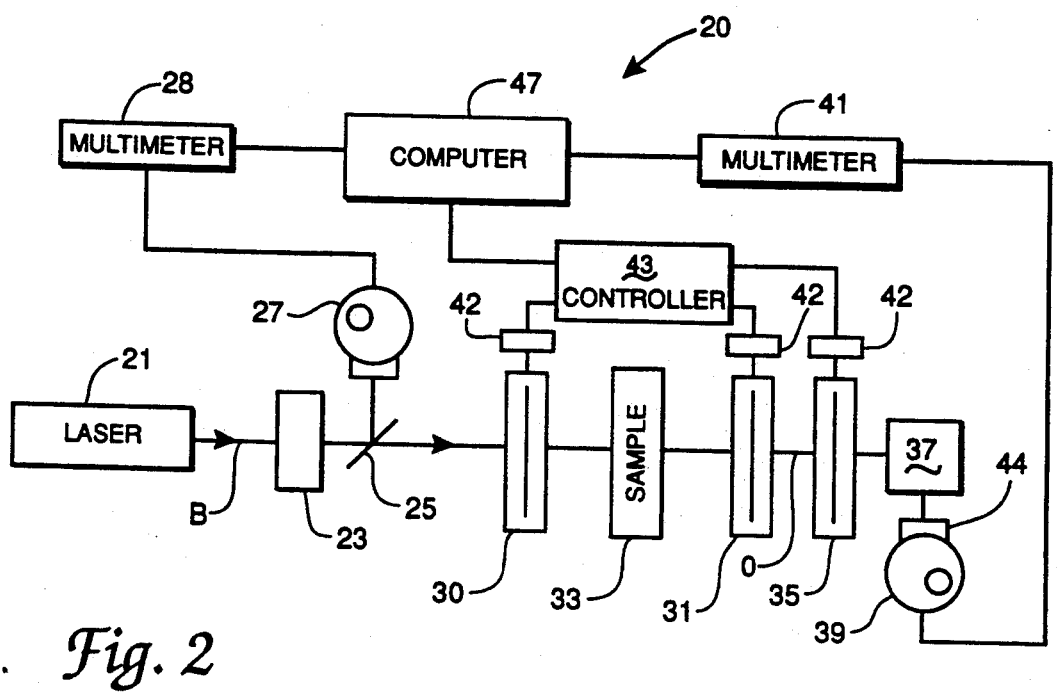
FIG. 2 is an illustration of the component parts of an infrared laser polarimeter system built for demonstration of the invention.

FIG. 2 shows schematically the component parts of an infrared laser polarimeter system 20 built and operated in demonstration of the invention. Laser source 21 comprised a $CO_2$ laser projecting beam B (10.6 $\mu$m) along optical axis O. Because the detector electronics used in the demonstration system required a modulated signal, a beam chopper 23 (about 1 kHz) was disposed along axis 0 as suggested in FIG. 2. Beamsplitter 25 was included to divert a portion of beam B to detector 27 and digital multimeter 28 for monitoring power output of laser source 21 and for determining if rapid fluctuations or drift of laser power occurs during data collection. Beam B then passes through retarders 30,31 with sample 33 therebetween and polarizer 35, and is detected by a small infrared integrating sphere 37 and an HgCdTe photoconductive detector 39 operatively connected to digital multimeter 41. Programmable rotary stage controller 43 senses and controls the rotation of retarders 30,31 and polarizer 35. In demonstration system 20, polarizer 35 was an infrared wire grid polarizer mounted on a rotary stage which was in turn mounted on a 5-axis positioner which controlled all five remaining degrees of freedom (x, Y, z, yaw, and pitch) and included a kinematic base so that the mounted element can be moved out of position and replaced without realignment. Retarders 30 and 31, also in rotary stages, are mounted in 5-axis positioners in like manner. Rotatable elements 30,31,35 are driven with DC motors 42 and have optical encoders with resolution control to 0.001° and 0.025° repeatability. Low noise preamplifier and DC power supply 44 provided bias voltage to detector 39 and output voltage for multimeter 41. Detector 39 was operated in its linear region. Computer 47 may be suitably programmed to monitor and analyze information output from multimeters 28,41 and to control operation of rotary stage controller 43 via an IEEE-488 bus.

Figure 3:
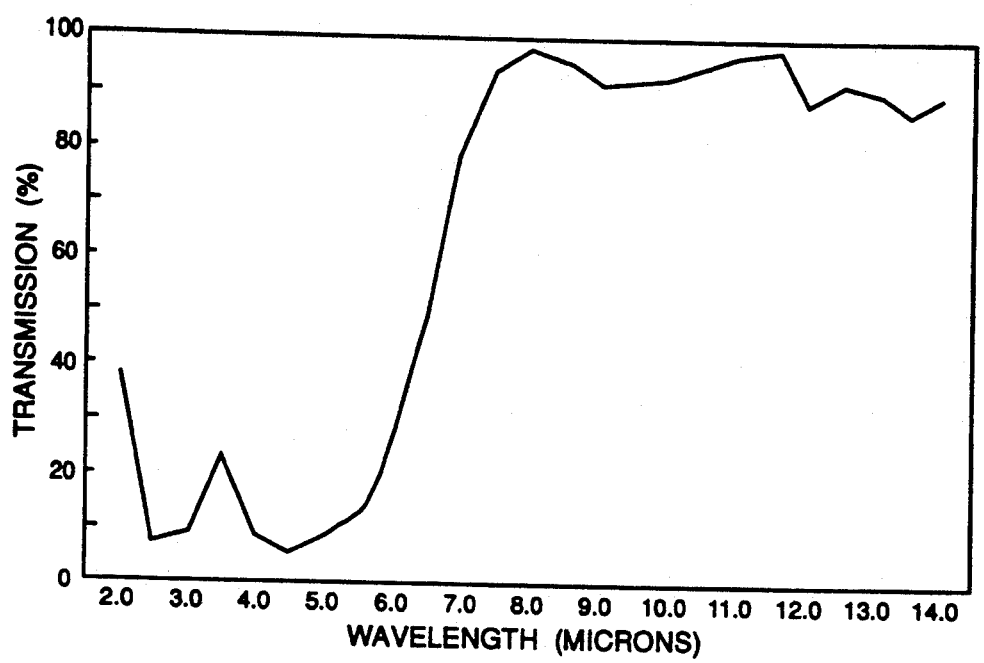
FIG. 3 is a transmission spectra of a wire grid polarizer included in the FIG. 2 system.

The invention may operate throughout the 3–14 μm region with minimum changes to the optical system provided the constituent polarizing elements are substantially achromatic, i.e. the polarization properties are nearly uniform as a function of wavelength. The laser polarimeter of the invention in any of the embodiments suggested herein may be easily modified by one skilled in the art guided by these teachings for use at substantially any specific wavelength of interest in the infrared, by substitution of suitable laser source, polarization elements and detector. Linear infrared polarizers which are readily commercially available include wire grid polarizers, crystal prism polarizers such as Glan-Thompson prisms and Brewster angle polarizers. A wire grid Polarizer has parallel lines of conducting material deposited on infrared-transparent substrates; polarization parallel to the lines is absorbed while polarization perpendicular to the lines is transmitted with little attenuation. Wire grid polarizers exhibit advantages over crystal polarizers and Brewster angle polarizers in the 3–14 μm spectral region, including compactness, high transmission, minimal beam offset or angular displacement at normal incidence, minimal polarization dependence of the ray angle through the polarizer and ready availability with large clear aperture. Accordingly, infrared wire grid polarizer 35 was used in the demonstration system 20 and comprised gold wire with wire spacing of 0.5 μm on a germanium substrate with an antireflection coating for the 8–14 μm wavelength region; the clear aperture of the polarizer was about 2.5 sq in. A transmission spectrum of the polarizer made on a Perkin-Elmer scanning infrared spectrophotometer, FIG. 3, shows the characteristic high transmission of the polarizer in the infrared. The extinction ratio of this element exceeds 1000:1.

Retarders 30,31 of system 20 comprised two rotating quarter wave cadmium sulfide zero order linear waveplates with 0.55 inch clear apertures and nominally 90° phase shift between orthogonal polarization states at 10.6 μm, and were selected to facilitate modulation of the various Mueller matrix elements onto intensity variations at separate modulation frequencies. The waveplate is a plane parallel plate of birefringement material with the crystal axis perpendicular to beam propagation direction and typically designed to operate ideally at a single wavelength. A wave plate with substantially any retardation value may be used, such as a quarter wave retarder, one-third wave retarder or other as would occur to the skilled artisan, but the intensity modulation which results using 90° phase shift (quarter waveplates) is preferred. Actual values supplied by the manufacturer for the specific retarders 30,31 were 89.7° and 88.0°, the compensation for which in system 20 is a novel feature of the invention. In the practice of the invention, retarder (waveplate) 31 was rotated at a rate five times that of retarder 30, which generates twelve harmonic frequencies in the Fourier spectrum discussed below; data is typically collected each 2–6° of rotation of retarder 31. The stages were stopped completely after each rotation increment. Alternatively, nonrotating modulators based on electrooptic effects may be used within the contemplation of the invention as variable retarders, and are controlled electrically to produce the phase shifts (retardances) equivalent to those produced by the physical rotation; this configuration may exhibit increased speed of data acquisition.

The (linear) polarization of laser source 21 provided initial polarization of beam B so that a linear polarizer between source 21 and sample 33 was not required. Retarders 30,31 and polarizer 35 were aligned relative to the polarization axis of laser source 21, which process may require considerable effort, and elimination of the remaining errors is another feature of the invention. A He-Ne laser was initially used to center each element individually of system 20 and to ensure that all elements are perpendicular to the beam; final alignment was accomplished after the He-Ne laser was replaced by $CO_2$ laser source 21. Retarders 30,31 were rotationally aligned using a blackbody source.

Figure 4:
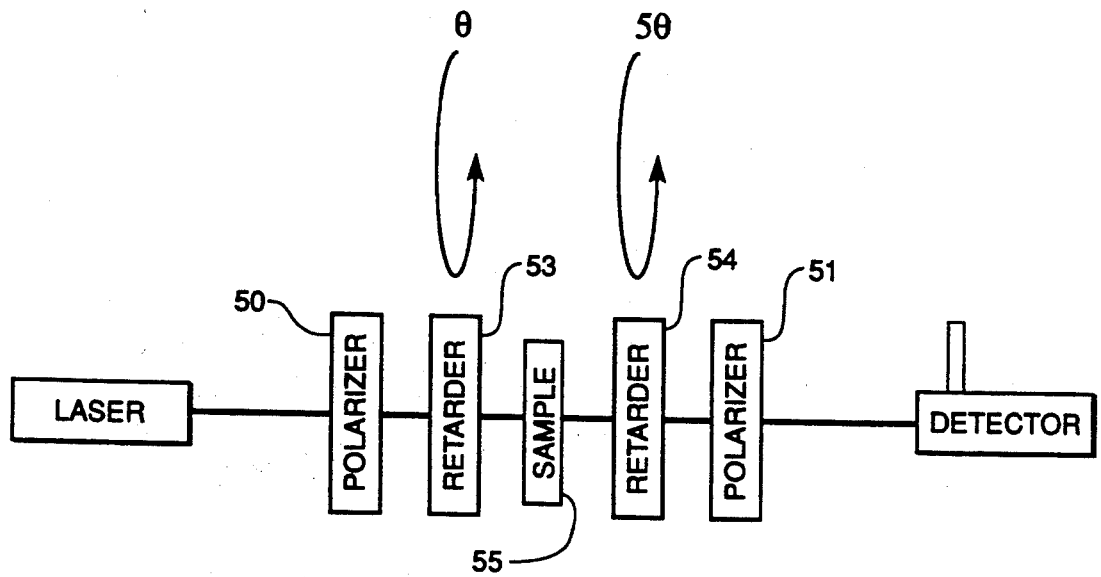
FIG. 4 illustrates polarizing elements and rotation rates.
Figure 5:
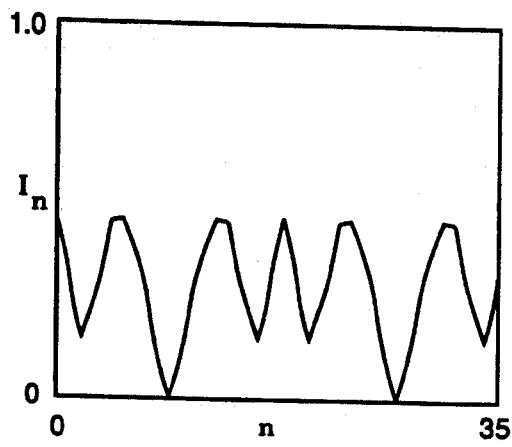
FIGS. 5-8 illustrate output beam intensity modulation for, respectively, no sample, a horizontal linear polarizer, a vertical linear polarizer, and a half waveplate at 45°.
Figure 6:
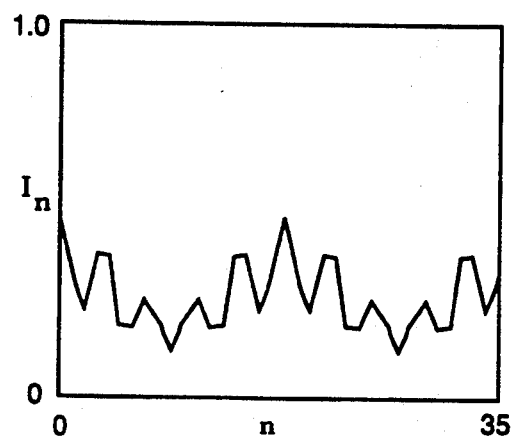
Figure 7:
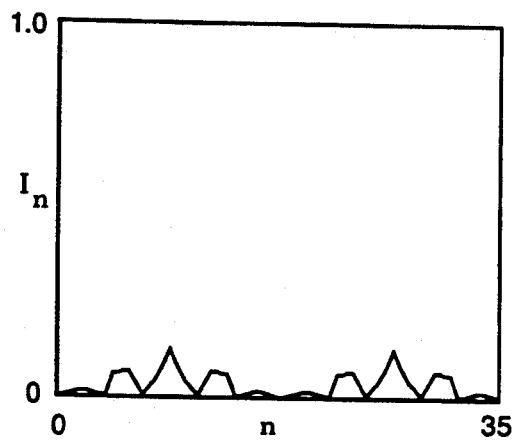
Figure 8:
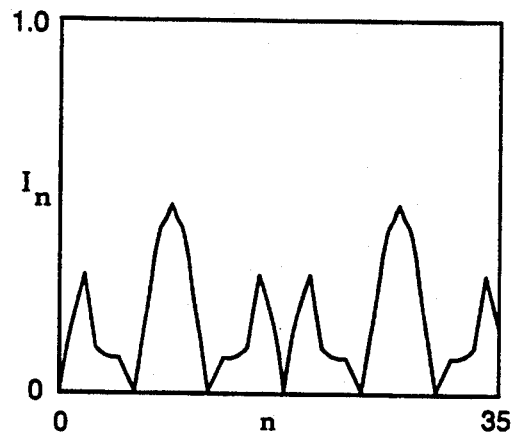

The Mueller matrix treatment and Fourier analysis of the output signal of the invention follows the analyses described in Azzam ("Photopolarimetric measurement of the Mueller matrix by Fourier analysis of a single detected beam", Opt Lett 2(6):148 (June 1978)), Goldstein et al ("Error Analysis of a Mueller matrix polarimeter", J Opt Soc Am 7(4):693 (Apr 1990)), and the cross reference, all of which, teachings are incorporated herein by reference. The invention in part implements the Mueller matrix treatment suggested by Azzam in a unique treatment for the determination of real errors (imperfections) in the system and for compensation for consequent measurement inaccuracies, such as in implementing a detection method using an integrating sphere (to compensate for beam wander), and a monitoring method for laser output power (to compensate for laser power fluctuations). Mueller matrix elements and Stokes vectors are used herein to represent, respectively, the polarization elements and polarized light. The Mueller matrix formation is preferable for experimental work requiring scattering and depolarization measurements. Two waveplates are rotated at different but harmonic rates and a modulation of the detected periodic intensity signal results at discrete intervals in angle. The Mueller matrix of the sample is found through a relationship between the Fourier coefficients of a series representing the modulation and elements of the sample matrix. Accordingly, the Mueller matrix for a generalized system using two aligned and fixed linear polarizers 50,51 and two rotating quarter wave retarders 53,54 as shown in FIG. 4 may be expressed as, $$P_2 R_2(\theta) M\, R_1(\theta) P_1$$

where $P_1, P_2$ characterize linear polarizers 50,51, $R_1, R_2$ characterize linear retarders 53,54 and M is sample 55. Substitution is then made of Mueller matrices for linear retarders with quarter wave retardation and a fast axis at 0° for $R_1$ and $R_2$, a horizontal linear polarizer $P_2$, a linear horizontal polarizer for $P_1$ (in practice, polarizer 50 is not needed if the laser source is polarized) and a sample for M. The matrices for the optical elements are tabulated in various references as functions of retardation and orientation angle (see e.g., W. A. Shurcliff, 20 *Polarized Light*, Harvard University Press, Boston (1962) or P. S. Theocaris et al, *Matrix Theory of Photoelasticity*, Springer Verlag, Berlin (1979)). The detected intensity through the sample is given by, $$I = c\, A\, M\, P$$

where $P = R_1 P_1 S$ is the Stokes vector of light leaving the polarizing Zoptics with S being the Stokes vector of light from the source, $A = P_2 R_2$ is the Mueller matrix of the analyzing optics, M is the Mueller matrix of the sample, and c is a proportionality constant obtained from the absolute intensity. Explicitly, $$I = c \sum_{i,j=1}^{4} a_i p_j m_{ij}$$

or, $$I = c \sum_{i,j=1}^{4} \mu_{ij} m_{ij}$$

where the $a_i$ are the elements of A, the $P_j$ are the elements of P, the $m_{ij}$ are the elements of the Mueller matrix M and where, $$\mu_{ij} = a_i p_j.$$

The order of multiplication can be changed because only the intensity is measured, i.e., the first element of the Stokes vector. Only the first row of matrix A is involved in the calculation, i.e., $$I = a_1(m_{11}p_1 + m_{12}p_2 + m_{13}p_3 + m_{14}p_4) +$$
$$a_2(m_{21}p_1 + m_{22}p_2 + m_{23}p_3 + m_{24}p_4) +$$
$$a_3(m_{31}p_1 + m_{32}p_2 + m_{33}p_3 + m_{34}p_4) +$$
$$a_4(m_{41}p_1 + m_{42}p_2 + m_{43}p_3 + m_{44}p_4)$$

The $\mu_{ij}$ are given by,
$\mu_{11} 1$
$\mu_{12} \cos^2 2\theta$
$\mu_{13} \sin 2\theta \cos 2\theta$
$\eta_{14} = \sin 2\theta$
$\mu_{21} = \cos^2 10\theta$
$\mu_{22} = \cos^2 2\theta \cos^2 10\theta$
$\mu_{23} = \sin 2\theta \cos^2 10\theta$
$\mu_{24} = \sin 2\theta \cos^2 10\theta$
$\mu_{31} = \sin 10\theta \cos 10\theta$
$\mu_{32} = \sin 2\theta \cos 2\theta \sin 10\theta \cos 10\theta$
$\mu_{33} = \sin 2\theta \cos 2\theta \sin 10\theta \cos 10\theta$
$\mu_{34} = \sin 2\theta \sin 10\theta \cos 10\theta$
$\mu_{41} = -\sin 10\theta$
$\mu_{42} = -\cos^2 2\theta \sin 10\theta$
$\mu_{43} = -\sin 2\theta \cos 2\theta \sin 10\theta$
$\mu_{44} = -\sin 2\theta \sin 10\theta$ when the rotation ratio is 5:1. These equations can be expanded in a Fourier series to yield the Fourier coefficients which are functions of the Mueller matrix elements.

The inversion of these relations gives the Mueller matrix elements $m_{ij}$ in terms of the Fourier coefficients:

$m_{11} = a_0 - a_2 + a_8 - a_{10} + a_{12}$
$m_{12} = 2a_2 - 2a_8 - 2a_{12}$
$m_{13} = 2b_2 + 2b_8 - 2b_{12}$
$m_{14} = b_1 - 2b_{11} 32\, b_1 + 2b_9 = b_1 + b_9 - b_{11}$
$m_{21} = -2a_8 + 2a_{10} - 2a_{12}$
$m_{22} = 4a_8 + 4a_{12}$
$m_{23} = -4b_8 + 4b_{12}$
$m_{24} = -4b_9 = 4b_{11} = 2(-b_9 + b_{11})$
$m_{31} = -2b_8 + 2b_{10} - 2b_{12}$
$m_{32} = 4b_8 + 4b_{12}$
$m_{33} = 4a_8 - 4a_{12}$
$m_{34} = 4a_9 = -4a_{11} = 2(a_9 - a_{11})$
$m_{41} = 2b_3 - b_5 = -b_5 + 2b_7 = (b_3 - b_5 + b_7)$
$m_{42} = ''4b_3 = -4b_7 = -2(b_3 + b_7)$
$m_{43} = -4a_3 = -4a_7 = 2(a_3 + a_7)$
$m_{44} = -2a_4 = 2a_6 = (a_6 - a_4)$

The 5:1 ratio is the lowest ratio at which the expressions for the Fourier coefficients may be inverted so that all sixteen Mueller matrix elements may be obtained. (Ratios of 6:1, 7:1 or higher may also be used.)

Mueller matrices for polarimeter modulation with no sample, with a horizontal linear polarizer, with a vertical linear polarizer, and with a half wave plate at 45° may be ideally expressed respectively as, $$\begin{bmatrix} 1 & 0 & 0 & 0 \\ 0 & 1 & 0 & 0 \\ 0 & 0 & 1 & 0 \\ 0 & 0 & 0 & 1 \end{bmatrix}, \begin{bmatrix} 0.5 & 0.5 & 0 & 0 \\ 0.5 & 0.5 & 0 & 0 \\ 0 & 0 & 0 & 0 \\ 0 & 0 & 0 & 0 \end{bmatrix},$$

$$\begin{bmatrix} 0.5 & -0.5 & 0 & 0 \\ -0.5 & 0.5 & 0 & 0 \\ 0 & 0 & 0 & 0 \\ 0 & 0 & 0 & 0 \end{bmatrix}, \begin{bmatrix} 1 & 0 & 0 & 0 \\ 0 & -1 & 0 & 0 \\ 0 & 0 & 1 & 0 \\ 0 & 0 & 0 & -1 \end{bmatrix}.$$

Theoretical polarimeter intensity patterns are shown for these elements, respectively, in FIGS. 5–8.

Referring again to system 20 of FIG. 2, intensity values in the form of voltages were measured as retarders 30,31 were advanced incrementally through 180° and 900°, respectively. The Fourier coefficients are obtained from measured intensity values, and the solution may be obtained by any of several methods. For example, if, $$xa = I$$

where I is a vector of 36 (for 5° increments through 180°) intensity values, a is the set of 25 Fourier coefficients, and x is a 36×25 matrix where each row is of the form, $$1 \ \cos2\theta \cos4\theta \cos24\theta \sin2\theta \sin4\theta \sin24\theta$$

then the solution is, $$a = (x^T x)^{-1} x^T I$$

This is equivalent to the least squares solution, and the expression for the instrument response is, $$I(\theta) = a_o + \sum_{j=1}^{12} a_j \cos2j\theta + b_j \sin2j\theta$$

A factor of two appears with $\theta$ in the expansion because polarization elements repeat the behavior twice in one revolution, the actual measurement $\Phi(\theta)$ may be different from this value, the sum of the squares of these differences may be formed, viz., $$\sum_{l=0}^{35} (\Phi(\theta_l) - I(\theta_l))^2 = E(a_0, a_1, \ldots a_{12}, b_1, \ldots b_{12})$$

where E is a function of the coefficients and l is the subscript of the retarder angle. The values of the coefficients can now be found by setting the partial derivatives of E with respect to the coefficients equal to zero, i.e., $$\frac{\delta E}{\delta a_k} = 0, \quad \frac{\delta E}{\delta b_k} = 0$$

The expression then becomes for the derivative with respect to $a_1$, $$\sum_{l=0}^{35} (\Phi(\theta_l) - \left( a_0 + \sum_{j=1}^{12} (a_j \cos2j\theta_l + b_j \sin2j\theta_l) \right)(-2\cos2k\theta_l) = 0$$

Solving this system of 25 equations in 25 unknowns gives the least squares solution for the coefficients.

In the immediately foregoing analysis, effects of retardation in the polarizers and polarization in the retarders, and angular errors associated with the stages which rotate these elements are ignored. Only the relative orientations of the polarizers and retarders are considered relevant, and the analysis is simplified by measuring all angles relative to the polarization of the laser. The three polarization elements may have errors associated with their initial azimuthal alignment with respect to the laser polarization. In addition, one retarder or both may have retardances different from a quarter wave. In general, both retarders will have different retardances and the three polarization elements will be misaligned in azimuth. Error analysis associated with a Mueller matrix polarimeter is presented in Goldstein et al referenced above.

Calibration of the system of the invention is critical because orientational alignment errors of polarizing elements can induce errors in the resultant measured Mueller matrices. Different combinations of alignment errors produce errors in different sets of Mueller matrix elements. The sample matrix is the identity matrix when there is no sample in the polarimeter. If all but diagonal elements in the sample Mueller matrix are set equal to zero then all odd Fourier coefficients become zero. Since the diagonal elements are all equal to 1, the coefficients of the 12th harmonic vanish also. The 4th and 6th Fourier cosine coefficients are useless in solving for errors because they are not error dependent. This leaves coefficients $a_0$, $a_2$, $a_8$, $a_{10}$, $b_2$, $b_4$, $b_6$, $b_8$ and $b_{10}$, which are functions of the errors as follows:

$$a_0 = \tfrac{1}{4} + (1 - \epsilon_1)(1 - \epsilon_2)/16$$
$$a_2 = (1 + \epsilon_1)(1 - \epsilon_2)/16 + (1 + \epsilon_1)(1 - \epsilon_2)\epsilon_3\epsilon_5/2$$
$$a_8 = (1 + \epsilon_1)(1 + \epsilon_2)/16$$
$$a_{10} = (1 - \epsilon_1)(1 + \epsilon_2)/16$$
$$b_2 = -(1 + \epsilon_1)(1 - \epsilon_2)\epsilon_3/4 + (1 + \epsilon_1)(1 - \epsilon_2)\epsilon_5/8$$
$$b_4 = (\epsilon_4 - \epsilon_3 - \epsilon_5)/4$$
$$b_6 = (\epsilon_5 - \epsilon_3 - \epsilon_4)/4$$
$$b_8 = -(1 + \epsilon_1)(1 + \epsilon_2)(2\epsilon_4 - 2\epsilon_3 - \epsilon_5)/8$$
$$b_{10} = -(1 - \epsilon_1)(1 + \epsilon_2)(2\epsilon_4 - \epsilon_5)/8$$

These equations can be solved for the errors in terms of the Fourier coefficients. The equations for $a_0$ and $a_{10}$ yield, $$\epsilon_1 = 3 - 8(a_0 + a_1)$$

$$\epsilon_2 = \frac{4(a_0 - a_{10}) - 1}{1 - 4(a_0 + a_{10})}$$

The equation for $a_8$ with the equations for $a_0$ and $a_{10}$ give, $$\epsilon_1 = \frac{(a_8 - a_0)}{(a_8 + a_{10})}$$

$$\epsilon_2 = 8(a_8 + a_{10}) - 1$$

Adding the equations for $b_4$ and $b_6$ gives, $$\epsilon_3 = -2(b_4 + b_6)$$

The equation for $b_2$ can now be used to obtain, $$\epsilon_5 = \frac{8 b_2}{(1 + \epsilon_1)(1 - \epsilon_2)} + 2\epsilon_3$$

and finally taking the difference between $b_4$ and $b_6$ results in, $$\epsilon_4 = \epsilon_5 + 2(b_4 - b_6)$$

These values for errors are now to be substituted back into the equations for the Mueller matrix elements given in Goldstein et al referenced above using measured values of the Fourier coefficients.

The invention is therefore a polarimeter for obtaining the Mueller matrix of a sample of transmissive material having natural or induced birefringence (commonly evoked by applying an electric or magnetic field). The invention provides polarization and material property information at specific selected wavelengths with high spectral resolution. Fundamental constants of materials, such as the linear or nonlinear electro-optic tensor coefficients and the Verdet constant, may be obtained with measurement of the Mueller matrix with applied fields. Note that polarimeter data comprising less than the complete Mueller matrix may obtainable using the invention. For example, retardance and diattenuation of a sample are obtainable where only the sample is rotated. The invention exhibits advantages over existing polarimeters in measuring the entire Mueller matrix, makes these measurements in the infrared, and is constituted for compensating for major error sources (beam wander, nonideal retarders, element orientation misalignments).

The invention therefore provides an infrared laser polarimeter system for making measurements of electro-optical properties of material samples at specific laser wavelengths. It is understood that modifications to the invention may be made as might occur to one skilled in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

I claim:

1. An infrared laser polarimeter system, comprising:
   (a) a source of infrared laser radiation for projecting a laser beam of preselected wavelength along an optical axis;
   (b) at least one polarizer disposed along said optical axis for linearly polarizing said laser beam and producing an output beam for analysis;
   (c) first and second rotatable optical retarders disposed along said optical axis between said source and said at least one polarizer, said optical retarders defining a sample region therebetween;
   (d) means for controllably rotating said second rotatable optical retarder at a second preselected rate greater than a first preselected rate for said firs optical retarder;
   (e) light collection means including an integrating sphere for collecting said output beam for analysis; and
   (f) detection means for analyzing said output beam.

2. The system of claim 1 wherein said second preselected rate of rotation of said second optical retarder is at least five times said first preselected rate of said first optical retarder.

3. The system of claim 1 wherein said source of infrared laser radiation is a laser selected from the group consisting of $CO_2$, CO, HeNe and HF.

4. The system of claim 3 wherein said source of infrared laser radiation has a preselected wavelength in the range of 3 to 14 microns.

5. The system of claim 1 wherein said at least one polarizer is one of a wire grid polarizer and a crystal prism polarizer.

6. The system of claim 1 wherein each of said retarders comprises a waveplate.

7. The system of claim 1 further comprising a beam chopper disposed along said optical axis for modulating said beam.

* * * * *